US009881126B2

(12) United States Patent
Alvarez Del Castillo et al.

(10) Patent No.: US 9,881,126 B2
(45) Date of Patent: Jan. 30, 2018

(54) ARRANGEMENTS FOR VIEWING CLINICAL IMAGES

(71) Applicant: Siemens Medical Solutions USA, Inc., Malvern, PA (US)

(72) Inventors: Joan Alvarez Del Castillo, Oxford (GB); Kevin Scott Hakl, Oxford (GB); Christian Mathers, Oxford (GB); Abhinav Shanker, Oxford (GB)

(73) Assignee: Siemens PLC, Camberley (GB)

( * ) Notice: Subject to any disclaimer, the term of this patent is extended or adjusted under 35 U.S.C. 154(b) by 547 days.

(21) Appl. No.: 14/556,496

(22) Filed: Dec. 1, 2014

(65) Prior Publication Data
US 2015/0154356 A1  Jun. 4, 2015

(30) Foreign Application Priority Data
Nov. 29, 2013 (GB) .................................. 1321153.7

(51) Int. Cl.
 G06F 15/00 (2006.01)
 G06F 13/00 (2006.01)
 G06F 19/00 (2011.01)
(52) U.S. Cl.
 CPC ................................ G06F 19/321 (2013.01)
(58) Field of Classification Search
 CPC ............................ G06T 7/00; G06T 11/005
 USPC ........................................ 715/715, 700, 853
 See application file for complete search history.

(56) References Cited

U.S. PATENT DOCUMENTS

| 8,396,268 | B2* | 3/2013 | Zabair | G06K 9/00 382/128 |
| 2008/0181472 | A1* | 7/2008 | Doi | G06T 7/00 382/128 |
| 2008/0240533 | A1* | 10/2008 | Piron | G01R 33/482 382/131 |
| 2013/0004042 | A1* | 1/2013 | Yang | G06T 11/005 382/131 |
| 2013/0121555 | A1* | 5/2013 | Bruder | G06T 11/003 382/131 |

FOREIGN PATENT DOCUMENTS

WO  WO 02025588 A2  3/2002

OTHER PUBLICATIONS

Strickland, N.H. et al.: "Design for the optimal arrangement of magnetic resonance images on PACS monitors"; in SPIE-Int. Soc. Pot.; 1997; pp. 432-439; vol. 3031; ISSN 0277-786X; GB.

* cited by examiner

Primary Examiner — Kevin Nguyen
(74) Attorney, Agent, or Firm — Schiff Hardin LLP (57) ABSTRACT

In a method and system for populating multi-segment layouts with related multimodal medical images, a relationship is determined between subsets of the multimodal medical images. The relationship is used to determine selected subsets initially selected for display in respective segments of a segmented display. Appropriate images relating to selected subsets are used to populate the remaining display segments.

22 Claims, 5 Drawing Sheets

ARRANGEMENTS FOR VIEWING CLINICAL IMAGES

BACKGROUND OF THE INVENTION

The present invention relates to arrangements for viewing clinical images. It is particularly concerned with arrangements which allow simple selection of images for viewing together, selected from among a large collection of image data representing different imaging modalities captured at different times.

In the present description, the following terms may carry the following meanings, or equivalents thereof:

Time Point—A collection of acquisitions pertaining to one clinically relevant period in time.

Acquisition—A collection of reconstructions pertaining to one clinical examination, this may be multiple series in one study or a subset of the series in a study, but will have all been taken on the same scanner and be tied to the same combination of raw data.

Scan—a data acquisition event in which a patient is placed in scanner and a protocol is run which results in numerous series (reconstructions) being created.

Reconstruction—A set of images that have been derived from a scan.

Recon—A reconstruction.

Layout—A specific organization of images on a display.

Segment—A view which may display a single image, or it may show a 3D re-projection created from multiple original images, or a segment may contain an image like fusion comprised from two different series.

Hanging protocol—The organization of images in a clinical radiographic presentation.

Series—One or more 2D or 3D images. In the case of oncology procedures these will often be slices of the same volume which the system will then interpret as a 3D volume of the patient and project and display in myriad ways back to the physician.

Study—A collection of series.

Registration—A process of aligning two volumes or images such that they are well correlated.

DICOM—Digital Imaging and Communications in Medicine: explained further at dicome.nema.org.

Extent—the proportion of a patient's body represented in an image

Clinicians have to compare data that has been acquired in different coordinate systems, using different modalities and at different times in order to provide a complete clinical interpretation. The following example mixtures of data are commonly read in a single sitting for evaluating image data for a single patient:

1. Data reconstructed in different ways from a single set of scan data, for example different CT slice thickness reconstructions;
2. data acquired in different modalities, but at a same time—known as "co-acquired data"—such as PET and CT data acquired in a combined CT/PET scanner;
3. Sequentially acquired body regions in a same modality, for example CT data representing a patient's thorax followed by CT data representing the same patient's abdomen;
4. Fast sequential acquisitions of data, such as multi-phase CE CT;
5. Temporally-related but separate volumes from a single acquisition, such as Dynamic PET;
6. Collections of data for a long term comparisons, for example, sets of corresponding data taken pre- and post-treatment.

In order to optimize a clinician's workflow, image combinations are typically prepared by a technician for viewing by the clinician. The data is conventionally read using a number of different hanging protocols or layouts. For example, the data may be correlated using side-by-side viewing or fusion. The images must be aligned to one another in order to provide a useful combination of information to the clinician.

The richness and complexity of this data means that the preparation for a clinical read is often a time-consuming manual process, sometimes taking longer than the clinical interpretation of the data once visualized. With the advent of "advanced imaging" the number of presentation parameters that need to be specified for each image displayed on the screen has also dramatically increased. Overall this forms a barrier to the key task of the clinician which is to visually interpret these images.

SUMMARY OF THE INVENTION

The present invention addresses the problem of providing a display layout for multiple data sets for simultaneous reading.

This problem is addressed in accordance with the invention by selecting appropriate images for efficient clinical evaluation by a method that includes the following steps, and a system for executing such a method.

1. Data assignment to a number of hierarchical abstract placeholders for the clinical use of the data.
2. Layouts are created, modified and saved with placeholders marked for all segments based on the placement of placeholders into the layout by the user.
3. A user may select certain image data for display, such as an individual reconstruction. On loading the selected certain image data, data is assigned to each placeholder, which most closely corresponds to the characteristics of the placeholders and may be presented to the user alongside a hierarchical representation of the placeholders.
4. By selecting different certain image data, a user may adjust what is displayed in the layout, based upon the placeholder hierarchy. Examples include changing all data shown from a timepoint to corresponding data for a different timepoint, changing all data for an acquisition to corresponding data for a different acquisition, or changing all data shown for a reconstruction to corresponding data for a different reconstruction.

DESCRIPTION OF THE PREFERRED EMBODIMENTS

The present invention addresses the problem of selecting appropriate images for efficient clinical evaluation by a method including the following steps.

Figure 1:
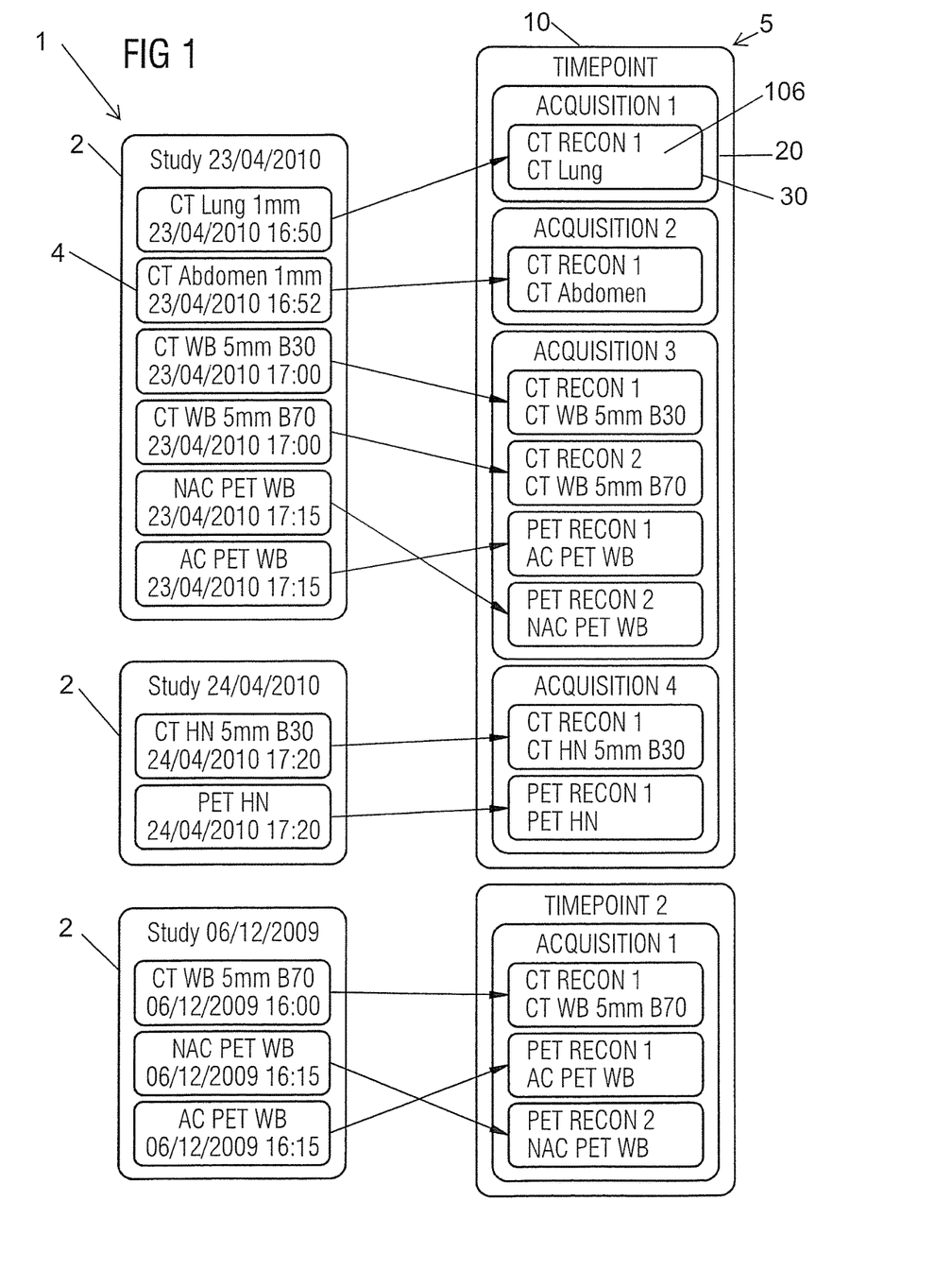
FIG. 1 illustrates an arrangement of a large number of acquired image data sets into a hierarchical structure identified by placeholders.

1. Data assignment to a number of hierarchical abstract placeholders for the clinical use of the data (FIG. 1).

Figure 2:
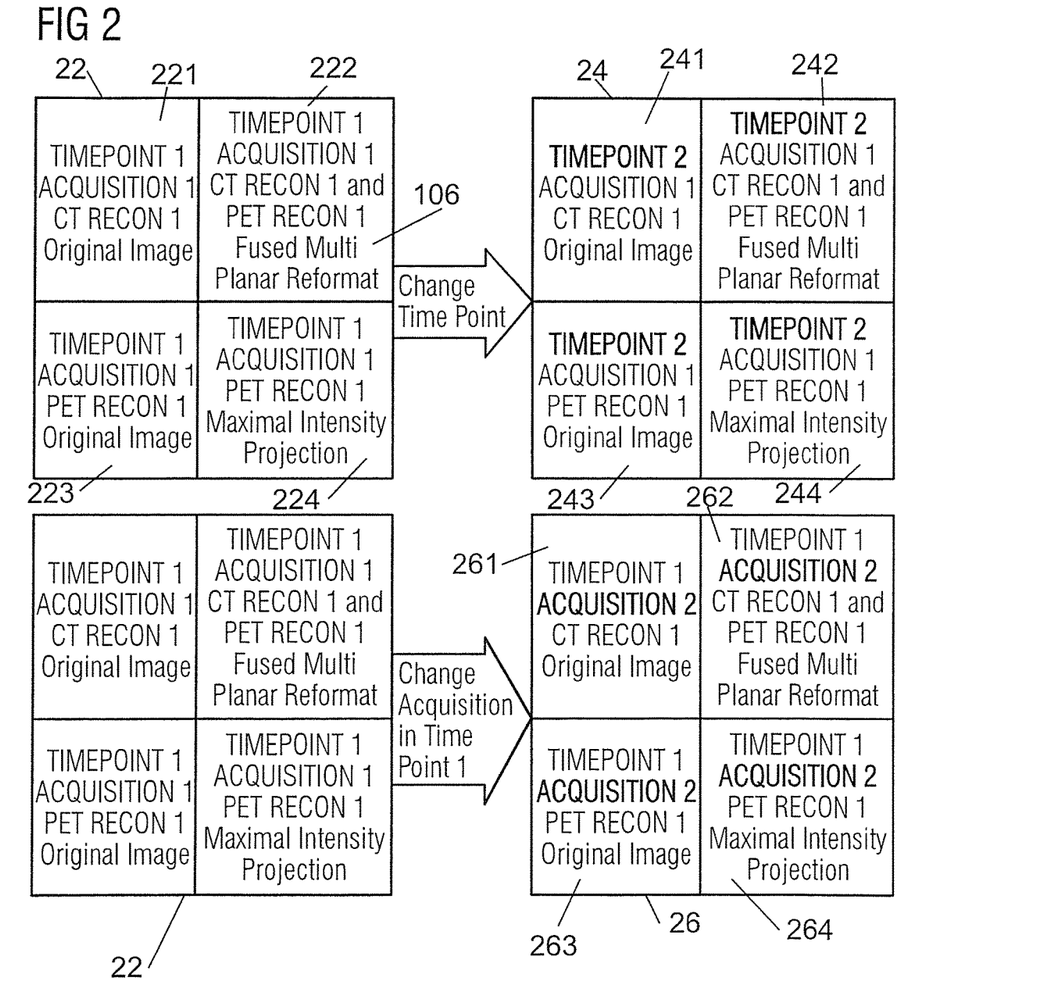
FIG. 2 illustrates a method of "drag and drop" exchanges between image data subsets according to an aspect of the present invention.

2. Layouts are created, modified and saved with placeholders marked for all segments based on the placement of placeholders into the layout by the user (FIG. 2).

Figure 5:
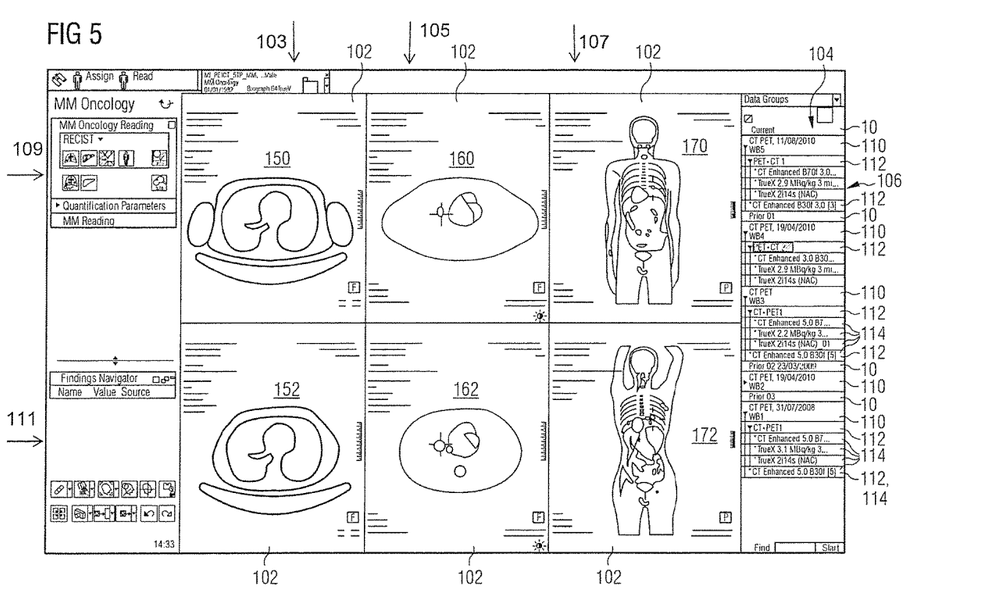
FIG. 5 shows an example screenshot of an image viewing arrangement according to an embodiment of the invention.

3. A user may select certain image data for display, such as an individual reconstruction. On loading the selected certain image data, data is assigned to each placeholder which most closely corresponds to the characteristics of the placeholders and may be presented to the user alongside a hierarchical representation of the placeholders (FIG. 5).

4. By selecting different certain image data, a user may adjust what is displayed in the layout, based upon the placeholder hierarchy. Examples include changing all data shown from a timepoint to corresponding data for a different timepoint, changing all data for an acquisition to corresponding data for a different acquisition, or changing all data shown for a reconstruction to corresponding data for a different reconstruction. Steps in such an adjustment are illustrated in FIGS. 2 and 5 and explained further below.

As shown in FIG. 1, image data is acquired in a number of studies 2 each including a number of data capture sessions 4. Within each study, image data may be captured in a plurality of modalities, a plurality of patient body regions, and a plurality of imaging parameter sets.

The image data is assigned to a hierarchical structure 5 of timepoints 10, acquisitions 20 and reconstructions 30. Each reconstruction is represented by a placeholder 106.

Typically, each study 2 will remain within a single timepoint 10. Images are first grouped into "timepoints" based on study 2 boundaries and time. Within each timepoint 10 images are grouped into acquisitions 20 based upon reconstructions derived from the same raw data, or from data co-acquired in the same session.

Each reconstruction 30 in an acquisition 20 which is part of a timepoint 10 is represented by a placeholder 106. FIG. 1 shows a mapping of data capture sessions 4 within studies 2 to timepoints 10, acquisitions 20 and reconstructions 30.

Selected placeholders may be associated with segments of a layout. The selected placeholders may share certain characteristics—timepoint, acquisition number, imaging modality, reconstruction type.

FIG. 2 shows two examples of this arrangement in action. In each of the four parts to the drawing, a display layout is represented, showing four placeholders 106. Each placeholder is labelled with timepoint, acquisition number, imaging modality, reconstruction type. In a first layout 22, a display is illustrated, where four placeholders have been positioned in respective segments to define the layout.

Layout 22 may be changed to layout 24 in response to just changing one characteristic of one placeholder. In this example, the first placeholder 221 of layout 22 is replaced by first placeholder 241 of layout 24. Placeholder 241 differs from placeholder 221 in that it relates to 'timepoint 2' rather than 'timepoint 1'. All other characteristics are unchanged. The remaining placeholders 242, 243, 244 of layout 24 are changed in a corresponding way: "timepoint 1" is changed to "timepoint 2" and the other characteristics are unchanged. If such a placeholder corresponds to an actual reconstruction present in the current data set, see FIG. 1, then the corresponding reconstruction is displayed on the corresponding segment of the layout 24.

If any of the changed placeholders do not correspond to an actual reconstruction present in the current data set, see FIG. 1, then a "next-most-similar" reconstruction must be identified by a predetermined algorithm. For example, a reconstruction of a neighbouring timepoint but having remaining characteristics the same may be deemed to be the most similar. In the case illustrated with respect to layouts 22, 24, the corresponding reconstruction from layout 22 would be kept. Preferably, any reconstructions selected as "next-most-similar" should be identified as such by a label or colour cast on the display. Alternatively, the predetermined algorithm may define no reconstructions as "next-most similar", so that no image is displayed in a segment where the changed placeholder does not exactly correspond to an existing reconstruction.

In the upper part of FIG. 2 is represented a change in displayed images by selecting a placeholder representing a time point different from a presently-shown timepoint. All identifying parameters, in this case acquisition, reconstruction, modality, remain unchanged but the timepoint is replaced by the timepoint represented by the newly selected placeholder.

The lower part of FIG. 2 represents a similar change in displayed image data by newly selecting a placeholder representing an acquisition 30 different from a presently-shown acquisition, but within the same time point. In this case, the starting point is layout 22 as above. Placeholder 223 is replaced by a selected placeholder 263 which has a different acquisition number. Layout 26 results. Selected placeholder 263 takes the segment formerly occupied by placeholder 223, and the remaining segments 261, 262, 264 are taken by "next-most-similar" reconstructions, identified by a predetermined algorithm as discussed above. All other identifying parameters, in this case Timepoint, Recon, Modality, remain unchanged but the acquisition parameter is replaced by the acquisition parameter represented by the selected placeholder 263.

In other examples, the newly-selected placeholder may differ from the previous placeholder in more than one characteristic. In that case, all identifying parameters remain unchanged other than those which differ in the newly-selected placeholder. Those characteristics are changed for all placeholders to correspond to the values of the newly-selected placeholder.

Selection of a placeholder may be by a drag-and-drop method by a computer mouse or similar, selecting a placeholder from a hierarchy represented on-screen and "dropping" it onto the required segment of the display.

Each level of the hierarchy may be forced to match selection of lower levels from different parts of the hierarchy. For example, all the data in the layout which matches the time point of a segment may be linked. When one segment is changed by selecting a reconstruction from a different timepoint, all segments may try to update to show the same kind of data from the matching timepoint of the newly selected reconstruction.

Dropping a placeholder representing a series from a different time point and/or acquisition would result in data in the layout being replaced by data represented by similarly marked placeholder data from the time point and/or acquisition parameter of the dropped placeholder.

Alternative types of hierarchies may be provided and/or enforcement of changes in characteristics in only the most clinically relevant groupings. The same notion of matching and linking of data could be applied for other groupings e.g. rather than timepoint and acquisition you could say "everything labelled as a Head" or "everything that is a delayed recon".

In some embodiments, anatomy detection can be used to supplement the assignment of acquisition bundles and then utilized for a stronger semantic link across time points. That is, the represented patient body region may be used as another characteristic of the placeholders. Such anatomy detection may be performed using anatomical landmarks to determine which parts of a body are represented in a certain image. The same functionality can be extended to image selection.

In addition to selecting reconstructions for display, the various representations need to be aligned to provide the most informative image representations to the user.

Another feature of the present invention relates to acquisition structuring for adjusting alignment between image data. This feature will be described with particular reference to FIGS. 3 and 4.

Registration algorithms may be used in a method for automating preparation of image data for viewing. Some data is implicitly aligned, for example between different modalities captured in a single scan, while other data requires additional alignment. For data requiring additional alignment, the selection of data used for registration can affect the quality of registration produced, for example the choice of either the PET or the CT from a PET/CT study. Overall this forms a barrier to the key task of the physician which is to visually interpret the images.

Conventional imaging systems allow the user to align pairs of images using automatic algorithms and via manual tools. In addition they allow the user to save registrations with the data. However, while such systems employ some existing relationships between the data—for example, whether the images originate in a same study or different studies, to select an appropriate registration technique, they do not employ other relationships, such as whether it was co-acquired or was reconstructed from same raw data.

Patient image data is assigned to placeholders as described above with reference to FIG. 1.

A first registration technique is performed based upon relationships between reconstructions which are inherent in the associated acquisitions and timepoints. Registrations between any two volumes of the data set may be derived from this inherent registration.

Figure 3:
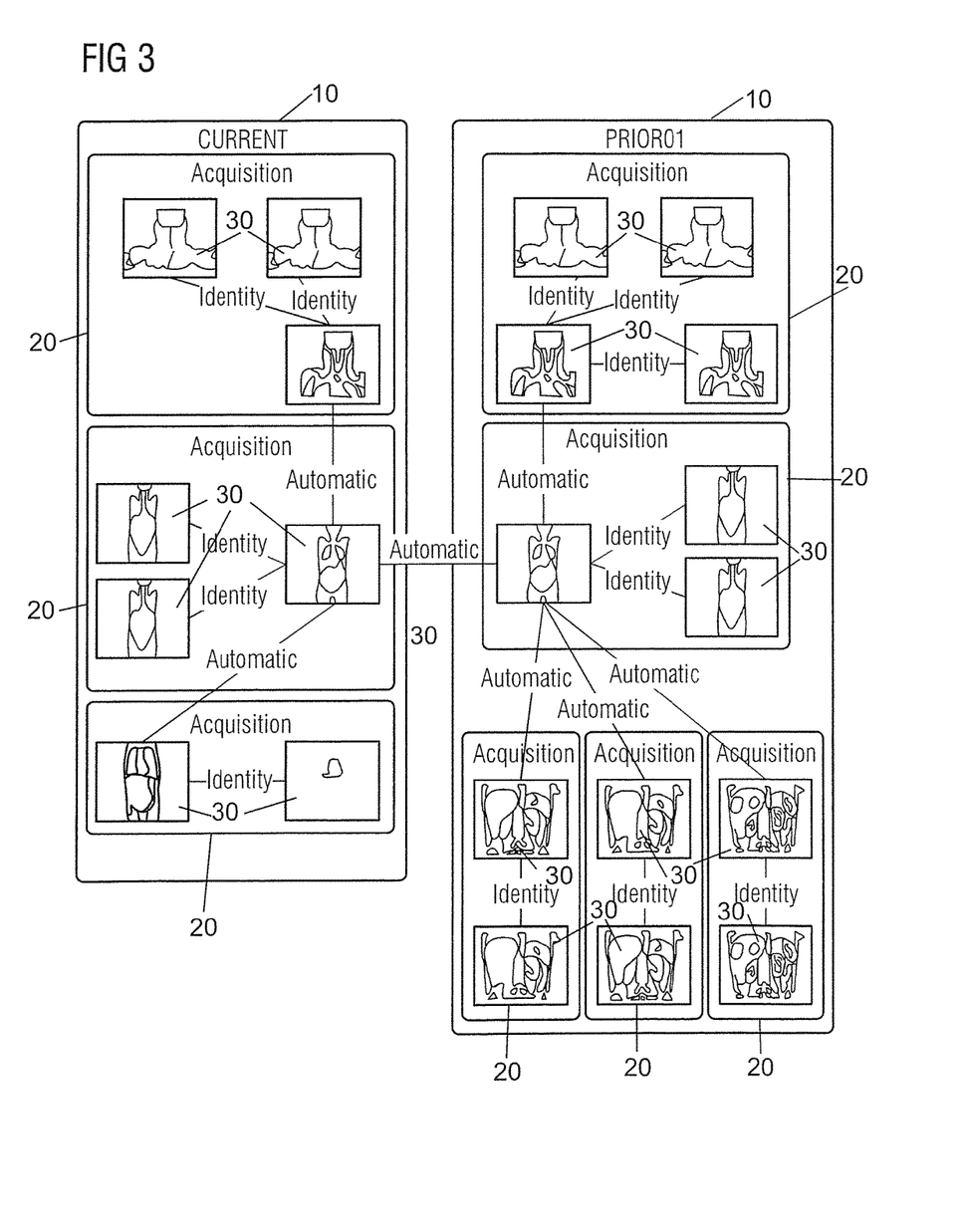
FIG. 3 illustrates a step in a method of registration between subsets of captured image data.

FIG. 3 illustrates an example of registration applied between data based on timepoint 10, acquisition 20 and reconstruction 30 hierarchy. Two time points 10 are represented: one labelled "CURRENT" and one labelled "PRIOR01".

Within each acquisition 20, the various reconstructions 30 are aligned by inherent alignment, as they are derived from a common dataset. This is represented in FIG. 3 as "identity". Within each timepoint 10, alignment between reconstructions may be performed by known automatic algorithms. As all relevant data is acquired at a single timepoint, the patient body represented will be essentially identical in each reconstruction. Such alignment by automatic algorithms is represented in FIG. 3 by "automatic".

Alignment of image data must also be performed between timepoints. For alignment between timepoints, the images with the largest extent are used for alignment between the time points, since such images should provide the greatest volume or area of alignment. In the second acquisition 20 in each timepoint 10, a full body image is shown. These two respective full-body images are aligned, and the remaining images within each timepoint are aligned to the respective full-body image.

Provision is preferably made for a user to change the registration between two series: in the following example, this is between two timepoints 10. This adjustment may update the effective registration for a number of series between acquisitions or between time points based upon the placeholder hierarchy such as represented in FIG. 3 or FIG. 1.

Figure 4:
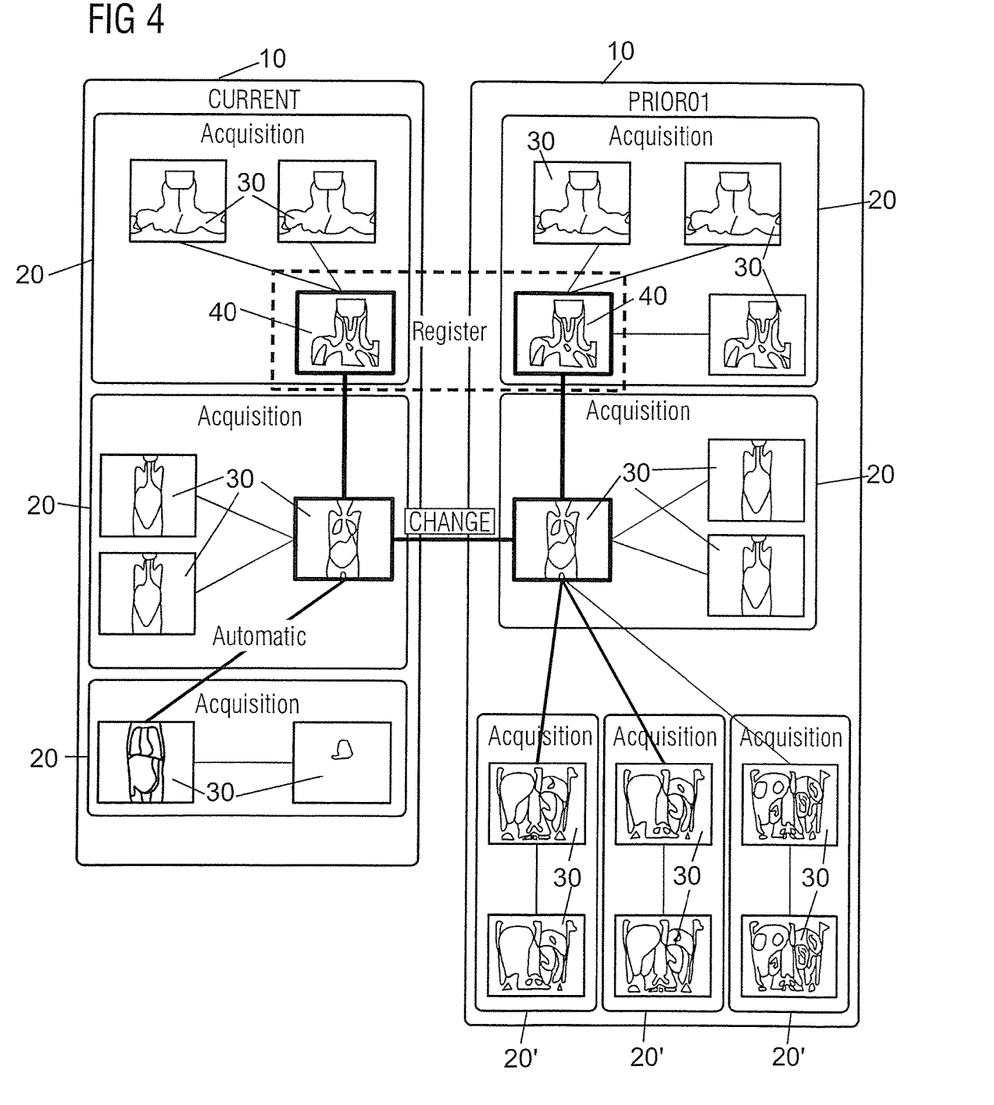
FIG. 4 illustrates a later step in the method of registration between subsets of captured image data.

FIG. 4 illustrates an example of such arrangements, in an embodiment of the present invention, in which the effect of changing the registration of two volumes in the hierarchy may be observed.

In this step, rather than maintaining the described alignment between full-body images as discussed with reference to FIG. 3, a user may decide to adjust alignment between the series to perform alignment based on head-and-neck series 40 in respective first acquisitions 20 of the two timepoints 10. The user selects the head-and-neck series 40 in each timepoint and an automated registration or alignment takes place. This is represented in FIG. 4 by a thick dashed line around the head-and-neck series 40 in each timepoint, and the label "register".

Any difference in registration between the original alignment using full-body images and the modified alignment using head-and-neck series 40 is used to modify inter-timepoint registration. All other series in each time point derive their inter-timepoint alignment from the alignment between full body images. By adjusting the inter-timepoint alignment of the full body images due to performing an alignment (registration) on the head-and-neck series 40 at each timepoint, the inter-timepoint alignment of the full-body images will be adjusted, causing all the series in both time points to have their inter-time point registration adjusted.

In the illustrated example, the change to registration between the head-and-neck images, represented by the label "register" in FIG. 4 causes a change in registration between the full-body images, labelled "CHANGE" in FIG. 4.

Images in further acquisitions 20' derive their inter-timepoint alignment from the alignment of the full-body images, and so their alignment will change accordingly.

In an embodiment, the placeholders 106 displayed in a layout are used as the sole source for the registration hierarchy for data. For example, data that is not displayed in the layout is not considered for the registration hierarchy. This would ensure that the minimum path of alignment steps is used to register all displayed data.

Acquisition logic may be provided to consider which patient anatomical regions are represented in each series. Such anatomical regions may be identified from image-based detection algorithms, to add an anatomical region parameter to the data hierarchy for registration. Such addition may improve correlation for similar body regions across studies an over long periods of time.

Examples of an image viewing arrangement and operating method according to certain embodiments of the present invention will now be described.

FIG. 5 shows a screen-shot of an image viewing arrangement of the present invention, in use. In this view, six segments 102 are shown, each displaying an image. A user may select more or fewer than six segments. A user may also define which images are displayed in each segment, for example by the drag-and-drop method mentioned above. In the illustrated arrangement, the left-hand column 103 of segments shows axial CT images, while the central column 105 shows axial PET images and the right-hand column 107 shows full-body MIP images.

At the far-right of the figure is shown a series navigator 104 showing a hierarchy of place holders 106, as discussed above with reference to FIG. 1. Each of the placeholders represents a subset of the images available for display. The placeholders 106 are grouped together into time-points 10.

Each timepoint 10 represents a user-determined grouping of one or more studies 110. Typically, each timepoint collects together all studies performed on a single day, or within a few days of one another. Each study includes at least one acquisition 112. Each study may include several series 114, or a study may represent a single series 114.

Each of the images in the upper row 109 of segments is selected from a first study, and represents a corresponding timepoint 10, labelled "current". The images selected for display are selected by defining a number of parameters, such as Timepoint 10, Acquisition 20, Reconstruction (location) 30, which together identify a single image from among the available images, for display in the corresponding segment 102. These parameters are shared among the segments. All of the images on the upper row are selected to provide an optimal view of a selected feature, and which shares the defined parameters. In this example, each of the segments in the upper row 109 show respective views of a same feature, which is marked with cross-hairs in images 160, 170.

The lower row of segments 111 show images respectively corresponding to the modality and view of the respective image in the top row 109, but selected from images of a second study. This second study 110 may be included within the same timepoint 10 as the first study, or more usually belongs to a second timepoint. As shown, the images of the second row 111 of segments are automatically selected from among the images of the corresponding study to most closely correspond with the displayed images of the top row.

In FIG. 5, the images 162, 172 of the lower row also show cross-hairs which highlight the same location as that highlighted by cross-hairs in the top row.

Preferably, this is achieved by selecting the images displayed in the bottom row by using defined parameters of the images in the top row: Acquisition, Modality, Reconstruction (location) and so on. Those skilled in the art will recognise that other parameters and methods may be used to select the "best match" of one image in one study with an image in another study. This selection of images enables a clinician to readily compare the feature identified with cross-hairs at the respective timepoints and to rapidly form an opinion on the development of the identified feature.

In use, a user may change the viewing angles of the images in each segment 102, and may progress through image "slices" (reconstructions), for example using keyboard strokes, mouse clicks, tracking balls or other input devices. By sharing defined parameters or otherwise selecting corresponding images, corresponding selections of images will appear in the segments 102 representing the second study 111.

According to a feature of the present invention, corresponding images from a third study may be selected and displayed in place of the images 111 from the second study, or in place of images 109 from the first study, simply by selecting a placeholder 106 corresponding to the third study. In a preferred embodiment, this may be achieved by using a "drag and drop" operation of a mouse or similar pointing device, by selecting the placeholder representing the third study in the series navigator 104, dragging it into a segment 102 of a selected row and dropping it there. Such operation may be interpreted as a command to replace all of the currently-displayed images in that row with corresponding images selected from the third study and matching corresponding images in the other row.

A user may then navigate through various reconstructions of the respective studies as discussed above.

At each level of hierarchy, the placeholders 106 are identified, and one 3D volume or 2D image is manually or automatically chosen as the "best" or "most appropriate" to use for initial registration. Data from a new time point 10 will adopt the same registrations as used in a previous time point to ensure that all images are registered, and that a user may move through all subsets together. The actual registration algorithms used are conventional in themselves, and will be familiar to those skilled in the art.

An expected quality of registration may be taken into account when establishing a hierarchy of registration such as those illustrated in FIGS. 3 and 4. For example, inherent registration between different modalities captured at the same time and on a same scanner (labelled "identity" in FIGS. 3 and 4) may be assumed to be relatively good, while corresponding series of data obtained at different timepoints will have a much weaker inherent registration, and are less likely to be deemed to provide a "best" pair of images for initial registration in the example considered in FIG. 5.

The selection of a full body image for registration (FIG. 3) may be deemed "best" in many instances because it encloses the greatest extent, and so provides relevant registration points for many possible regions of interest for viewing. On the other hand, where specific images exist of the region of interest, such as the head-and-neck images 40 highlighted in FIG. 4, these may be the "best" images to use for registration. In fact, it may be preferred to use specially tailored registration algorithms targeted to images of the corresponding type, for example, a dedicated head-and-neck registration algorithm may be selected for use in the example of FIG. 4.

In the example shown in FIG. 5, the resolution of the respective images may be a significant factor. As the two CT images 150, 152 in the respective studies have a greater resolution than the other images, the CT images may be chosen as "best" for inter-timepoint registration. The PET images 160, 162 and the MIP images 170, 172 may then be registered to the respective CT images 150, 152. Four images 160, 150, 152, 162 may then be registered together by performing only three registration calculations. When a user scrolls through reconstructions (slices) in one segment 102, the images in the other segments follow suit. This is enabled by registration between the various subsets of images represented by the placeholders 106 discussed above.

Registration between the different data series, acquisitions, studies and timepoints is required to define a spatial relationship between the images, and to enable a user to move between one image and the next in one segment and have the other images follow, to maintain a coherent view of corresponding features on all segments.

While the above-described example uses two rows 109, 111 of three images, other arrangements and numbers of segments 102 may be used and arranged as preferred. However, in each case, one subset 109 displays corresponding images from a first study while a second subset 111 displays corresponding images from a second study. In some embodiments, third and further subsets may be provided, to display corresponding information from respective third and further studies.

An example of acquisition structuring for adjusting alignment will now be discussed with reference to FIG. 5.

The example screen shot shown in FIG. 5 includes CT images 150, 152, PET images 160, 162 and MIP images 170, 172. The upper row 109 of images corresponds to a first time point and the lower images 111 correspond to a second time point. Each of the displayed images 150, 152, 160, 162, 170, 172 is one image selected from multiple images of a corresponding study. Registration between these images is performed by selecting a "best" candidate from each study, performing registration between those images, and then performing registration between remaining images in each study and the selected "best" candidate. The "best" candidate is an image selected for optimal viewing of a feature selected by the user as being of interest. In the present example, the feature identified by cross-hairs in images 160, 162, 170, 172 is selected as being of interest. One axial PET view 160, 162 and one coronal MIP view 170, 172 in each timepoint is selected automatically or manually by a user as providing the best available view of the selected feature. In this example, the CT images 150, 152 are axial images corresponding to axial PET images 160, 162.

Such hierarchical registration is schematically illustrated in FIGS. 3-4, where initial registration (FIG. 3) is performed between the images representing the greatest extent—in this case the full-body images—while remaining images of each study are aligned to those full-body images, as discussed above.

As illustrated in FIG. 4, a user may decide to register head-and-shoulders images 40 of respective timepoints 10 together, which in this example are parts of different acquisitions 20, rather than the full-body images.

If a clinician is due to review image data relating to the head or neck, such hierarchical alignment, first of selected "best" images at different timepoints, then of the remaining reconstructions within the study with the selected "best" image may result in improved registration of the particular images the clinician wishes to review.

The full-body images may then be registered to the respective aligned "best" head-and-neck images. However, since the full-body and head-and-neck images were already registered together in the step represented in FIG. 3, there might not be any change in the resultant registration between them.

Other parts of the hierarchical registration of FIG. 3 remain, with images in other modalities and/or in other acquisitions being aligned to the full-body image. In other embodiments, for example, images in other modalities and/or in other acquisitions 20 may be aligned to the selected head-and-neck images 40.

While the present invention has been described with reference to an example view of segments 102 showing views in certain directions in certain modalities, the present invention may be applied to viewing of any desired combination of viewing directions and modalities, as is suitable for the clinical evaluation taking place.

Although the above-described examples provide registration between full sets of data at chosen timepoints, alternative implementations of the present invention may provide registration only between the images that are currently being viewed: in the example of FIG. 5, only the viewed images may be registered: CT 150 to CT 152, then PET 160 to CT 150, MIP 170 to CT 150, PET 162 to CT 152 and MIP 172 to CT 152, rather than aligning the complete studies which include the viewed images.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for display of medical image data, comprising:
    means for arranging data into a hierarchy of subsets, said data comprising data from a number of studies, each study comprising data from one or more data capture sessions, with data from each capture session being reconstructed to produce a reconstruction, said hierarchy comprising data arranged into multiple timepoint subsets that each pertain respectively to one clinically relevant period of time, the data within each timepoint subset being divided into multiple acquisition subsets that each pertain respectively to one clinical examination with the data within each acquisition being divided into one or more of said reconstructions; and
    means for displaying a selected subset of the medical image data from said hierarchy, said selected subject corresponding to the one or more of said reconstructions.

2. The system according to claim 1, further comprising:
    selection means for selecting a reconstruction of the one or more reconstructions, wherein the means for displaying is configured for displaying the subset of the medical image data in one or more segments corresponding to the selected reconstruction.

3. The system according to claim 2, wherein the selection means comprises:
    a display configured to display one or more placeholders representing the one or more reconstructions, respectively; and
    a selection device configured to:
        select a placeholder from the one or more displayed placeholders;
        associate the selected placeholder with a corresponding segment of the one or more segments.

4. The system according to claim 3, further comprising:
    calculating means for calculating an available placeholder from the one or more placeholders that is most similar to another placeholder of the one or more placeholders in another of the one or more segments;
    replacement means for replacing a previous placeholder of the one or more placeholders with the selected placeholder.

5. The system according to claim 3, wherein the replacement means is configured to modify one or more characteristics of the other placeholder of the one or more placeholders in a manner corresponding to one or more differences in characteristics between the selected placeholder and the previous placeholder to replace the previous placeholder of the one or more placeholders with the selected placeholder.

6. The system according to claim 1, further comprising:
    medical image data alignment means for performing alignment between respective subsets of the medical image data to:
        align the acquisitions to one another based on a selected reconstruction of the one or more reconstructions in each timepoint; and
        align remaining reconstructions of the one or more reconstructions within each acquisition based on the selected reconstruction.

7. The system according to claim 6, wherein the medical image data alignment means provides alignment between data of respective timepoints by automatic alignment of the selected reconstructions in corresponding acquisitions in the respective timepoints.

8. The system according to claim 3, wherein the display is configured to display images from the selected reconstruction within the associated segment of the one or more segments, further comprising:
    a scrolling command device configured to transition one or more of the displayed images through a sequence of images representing a corresponding sequence of planes within the selected reconstruction.

9. The system according to claim 3, wherein the display is configured to display images within the one or more segments, a first subset of the one or more segments including images from a first timepoint and a second subset of the one or more segments including images from a second timepoint.

10. The system according to claim 8, wherein the first subset of the one or more segments and the second subset of the one or more segments correspond in modality, orientation, and location, such that a feature of the medical image data set is visible in the displayed images from the first timepoint and the displayed images from the second timepoint.

11. The system according to claim 8, wherein the selection device is configured to select a second placeholder from the one or more displayed placeholders to display another subset of the medical image data in another of the one or more segments to provide a combination of segments most similar to the display of the subset of the medical image data prior to the selection of the a placeholder from the one or more displayed placeholders.

12. A method for arranging medical image data for display, comprising:
arranging data into a hierarchy of subsets, said data comprising data from a number of studies, each study comprising data from one or more data capture sessions, with data from each capture session being reconstructed to produce a reconstruction, said hierarchy comprising data arranged into multiple timepoint subsets that each pertain respectively to one clinically relevant period of time, the data within each timepoint subset being divided into multiple acquisition subsets that each pertain respectively to one clinical examination with the data within each acquisition subset being divided into one or more of said reconstructions; and
displaying a selected subset of the medical image data from said hierarchy, said selected subject corresponding to one or more of said reconstructions.

13. The method according to claim 12, further comprising:
selecting a reconstruction of the one or more reconstructions, wherein the displaying the subset of the medical image data includes displaying of the subset of the medical image data in one or more segments corresponding to the selected reconstruction.

14. The method according to claim 13, wherein the selecting the reconstruction of the one or more reconstructions comprises:
displaying one or more placeholders representing the one or more reconstructions, respectively;
selecting a placeholder from the one or more displayed placeholders; and
associating the selected placeholder with a corresponding segment of the one or more segments.

15. The method according to claim 14, further comprising:
calculating an available placeholder from the one or more placeholders that is most similar to another placeholder of the one or more placeholders in another of the one or more segments;
replacing a previous placeholder of the one or more placeholders with the selected placeholder.

16. The method according to claim 14, wherein the replacing the previous placeholder comprises:
modifying one or more characteristics of the other placeholder of the one or more placeholders in a manner corresponding to one or more differences in characteristics between the selected placeholder and the previous placeholder to replace the previous placeholder of the one or more placeholders with the selected placeholder.

17. The method according to claim 12, further comprising:
aligning respective subsets of the medical image data, comprising:
aligning the acquisitions to one another based on a selected reconstruction in each timepoint; and
aligning remaining reconstructions within each acquisition based on the selected reconstruction.

18. The method according to claim 17, wherein the aligning respective subsets of the medical image data further comprises:
aligning data of respective timepoints by automatic alignment of the selected reconstructions in corresponding acquisitions in the respective timepoints.

19. The method according to claim 14, further comprising:
displaying images from the selected reconstruction within the associated segment of the one or more segments;
transiting one or more of the displayed images through a sequence of images representing a corresponding sequence of planes within the selected reconstruction.

20. The method according to claim 14, further comprising:
displaying images within the one or more segments, a first subset of the one or more segments including images from a first timepoint and a second subset of the one or more segments including images from a second timepoint.

21. The method according to claim 20, wherein the first subset of the one or more segments and the second subset of the one or more segments correspond in modality, orientation, and location, such that a feature of the medical image data set is visible in the displayed images from the first timepoint and the displayed images from the second timepoint.

22. The method according to claim 20, further comprising:
selecting a second placeholder from the one or more displayed placeholders to display another subset of the medical image data in another of the one or more segments to provide a combination of segments most similar to the display of the subset of the medical image data prior to the selection of the a placeholder from the one or more displayed placeholders.

* * * * *